(12) United States Patent
Miller et al.

(10) Patent No.: US 10,347,380 B2
(45) Date of Patent: Jul. 9, 2019

(54) INTRA-OPERATIVE REGISTRATION OF ANATOMICAL STRUCTURES

(71) Applicant: Curexo Technology Corporation, Fremont, CA (US)

(72) Inventors: Denise A. Miller, Fremont, CA (US); Rose A. Cipriano, Fremont, CA (US); Li Lu, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 1141 days.

(21) Appl. No.: 14/205,092

(22) Filed: Mar. 11, 2014

(65) Prior Publication Data

US 2014/0278232 A1 Sep. 18, 2014

Related U.S. Application Data

(60) Provisional application No. 61/780,981, filed on Mar. 14, 2013.

(51) Int. Cl.
| | |
|---|---|
| *A61B 34/10* | (2016.01) |
| *A61B 90/00* | (2016.01) |
| *G06T 7/33* | (2017.01) |
| *G16H 50/50* | (2018.01) |

(52) U.S. Cl.
CPC ............. *G16H 50/50* (2018.01); *A61B 34/10* (2016.02); *G06T 7/337* (2017.01); *A61B 2034/101* (2016.02); *A61B 2090/364* (2016.02); *G06T 2207/30008* (2013.01)

(58) Field of Classification Search
CPC ......... A61B 90/36; A61B 34/20; A61B 32/20; A61B 5/0536; A61B 5/03; A61B 17/14; A61B 117/15; A61B 5/00; A61B 34/10; A61B 2034/101; A61B 2090/364; G01S 7/52073; G06T 7/00; G06T 7/0044; G06T 7/337; G06T 2207/30008; G16H 50/50
USPC ........ 606/102, 130; 600/407, 414, 424, 437, 600/547; 623/901
See application file for complete search history.

(56) References Cited

U.S. PATENT DOCUMENTS

| | | | |
|---|---|---|---|
| 5,871,018 A | 2/1999 | Delp et al. | |
| 6,006,126 A * | 12/1999 | Cosman ................ | A61B 34/20 600/414 |
| 6,033,415 A | 3/2000 | Mittelstadt et al. | |
| 6,205,411 B1 | 3/2001 | DiGioia, III | |

(Continued)

FOREIGN PATENT DOCUMENTS

WO 03061501 A3 7/2003

*Primary Examiner* — Regis J Betsch
*Assistant Examiner* — Kaleria Knox
(74) *Attorney, Agent, or Firm* — Avery N. Goldstein; Blue Filament Law PLLC

(57) ABSTRACT

Described herein are methods, systems and devices for image-guided, computer-assisted surgical procedures, in particular for intra-operative registration of anatomical structures. Embodiments of the invention may enable a user to register the surface of an anatomical structure intra-operatively in an interactive, computer-guided process. The user may send information about acquired data points to the computer, and the computer may evaluate the aggregate of data points, optionally provide instructions to the user for acquisition of additional data points, and signal to the user when sufficient data points have been acquired for registration of the surface of the anatomical structure.

17 Claims, 5 Drawing Sheets

(56) References Cited

U.S. PATENT DOCUMENTS

| | | | |
|---|---|---|---|
| 6,236,875 B1* | 5/2001 | Bucholz | A61B 5/0064 |
| | | | 600/407 |
| 6,381,485 B1* | 4/2002 | Hunter | G06T 3/0068 |
| | | | 324/244 |
| 6,430,434 B1 | 8/2002 | Mittelstadt | |
| 7,715,602 B2 | 5/2010 | Richard | |
| 2002/0136437 A1 | 9/2002 | Gerard et al. | |
| 2003/0225415 A1* | 12/2003 | Richard | A61B 90/36 |
| | | | 606/102 |
| 2004/0019263 A1* | 1/2004 | Jutras | A61B 34/20 |
| | | | 600/407 |
| 2008/0077158 A1* | 3/2008 | Haider | A61B 17/15 |
| | | | 606/130 |
| 2008/0114239 A1* | 5/2008 | Randall | G01S 7/52073 |
| | | | 600/437 |
| 2008/0255442 A1* | 10/2008 | Ashby | A61B 5/103 |
| | | | 600/407 |
| 2010/0198101 A1* | 8/2010 | Song | A61B 5/0536 |
| | | | 600/547 |
| 2011/0112397 A1* | 5/2011 | Shen | A61B 34/20 |
| | | | 600/424 |
| 2011/0160738 A1* | 6/2011 | McIntosh | A61B 8/565 |
| | | | 606/102 |

* cited by examiner

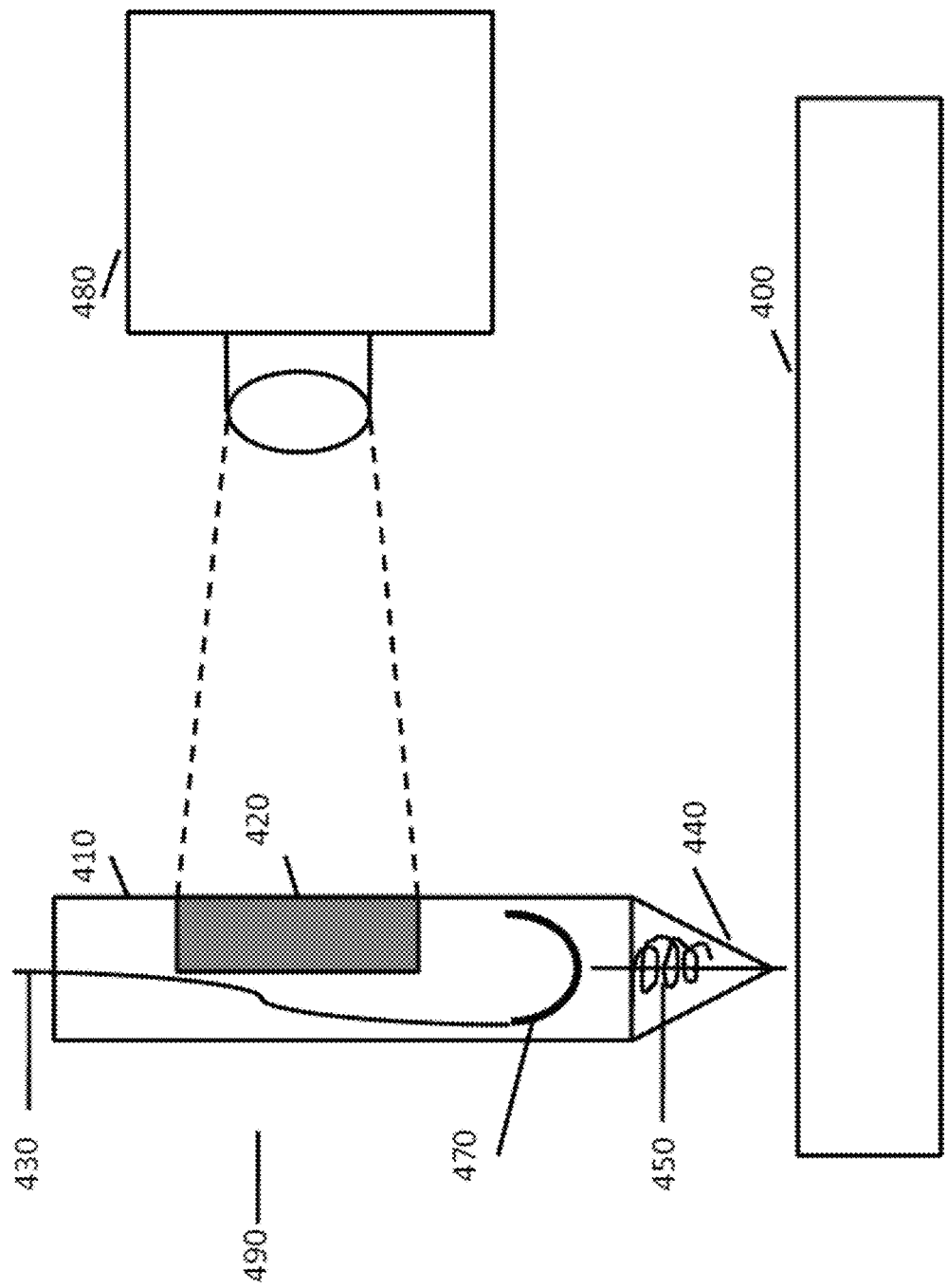

INTRA-OPERATIVE REGISTRATION OF ANATOMICAL STRUCTURES

RELATED APPLICATIONS

This application is a non-provisional application that claims priority benefit of U.S. Provisional application Ser. No. 61/780,891 filed 14 Mar. 2013; the contents of which are hereby incorporated by reference.

TECHNICAL FIELD

The present invention relates to methods, devices and systems for rapidly and efficiently achieving intra-operative alignment of anatomical structures with pre-operatively generated representations of the anatomical structures.

BACKGROUND

Image-guided computer-assisted robotic surgery has become a mainstay in many fields of surgery, particularly in orthopedic surgery. In the pre-operative planning phase of a surgery, representations of the anatomical structure of interest, such as a bone, are generated with medical imaging technologies, such as Computer Tomography (CT), Ultrasound (US) or Magnetic Resonance Imaging (MRI). However, in the intra-operative phase of the surgery, the position of the patient and the anatomical structure may have changed from the position in which the pre-operative representation was generated. In order for image guiding to function properly, the intra-operative position of the anatomical structures must be mapped to the pre-operative representation through a set of transformation parameters in a process called registration.

In current clinical practice this is often achieved by selecting a limited number of precisely located anatomical landmarks or surgically placed marker points, and matching their positions in the pre-operative and intra-operative representations. Because of the criticality of the location of these landmarks, the registration process is time consuming and prone to operator error. Therefore, surface recognition-based based algorithms have been developed, such as the Iterative Closest Point (ICP) and the Unscented Kalman Filter (UKF), which can analyze a large number of data points on a surface to achieve a match, or convergence, between the intra-operatively and pre-operatively generated representations of the surface.

Current clinical practice could be improved by incorporation of these technologies into a reliable, interactive and intra-operative procedure to map the surface of an anatomical structure to a previously generated representation to achieve registration of the surface.

SUMMARY OF THE INVENTION

The present invention relates to methods, devices and systems for rapidly and efficiently achieving intra-operative alignment of anatomical structures with pre-operatively generated representations of the anatomical structures. A computer-assisted method of registering a surface of an anatomical structure is provided that includes acquiring data points on the surface; evaluating quality of acquired data points; optionally rejecting unacceptable data points; collecting acceptable data points; evaluating quantity of acceptable data points; assessing if sufficient data points have been collected to achieve convergence of registration of the surface with a previously generated representation of the anatomical structure; optionally generating instructions for additional data points to be acquired; and optionally continuing acquiring data points at least until sufficient acceptable data points have been collected to achieve convergence of registration of the surface with a previously generated representation of the anatomical structure.

BRIEF DESCRIPTION OF THE DRAWINGS

FIG. 5 illustrates an embodiment of an acquisition probe and detector according to the invention.

DETAILED DESCRIPTION

Figure 1:
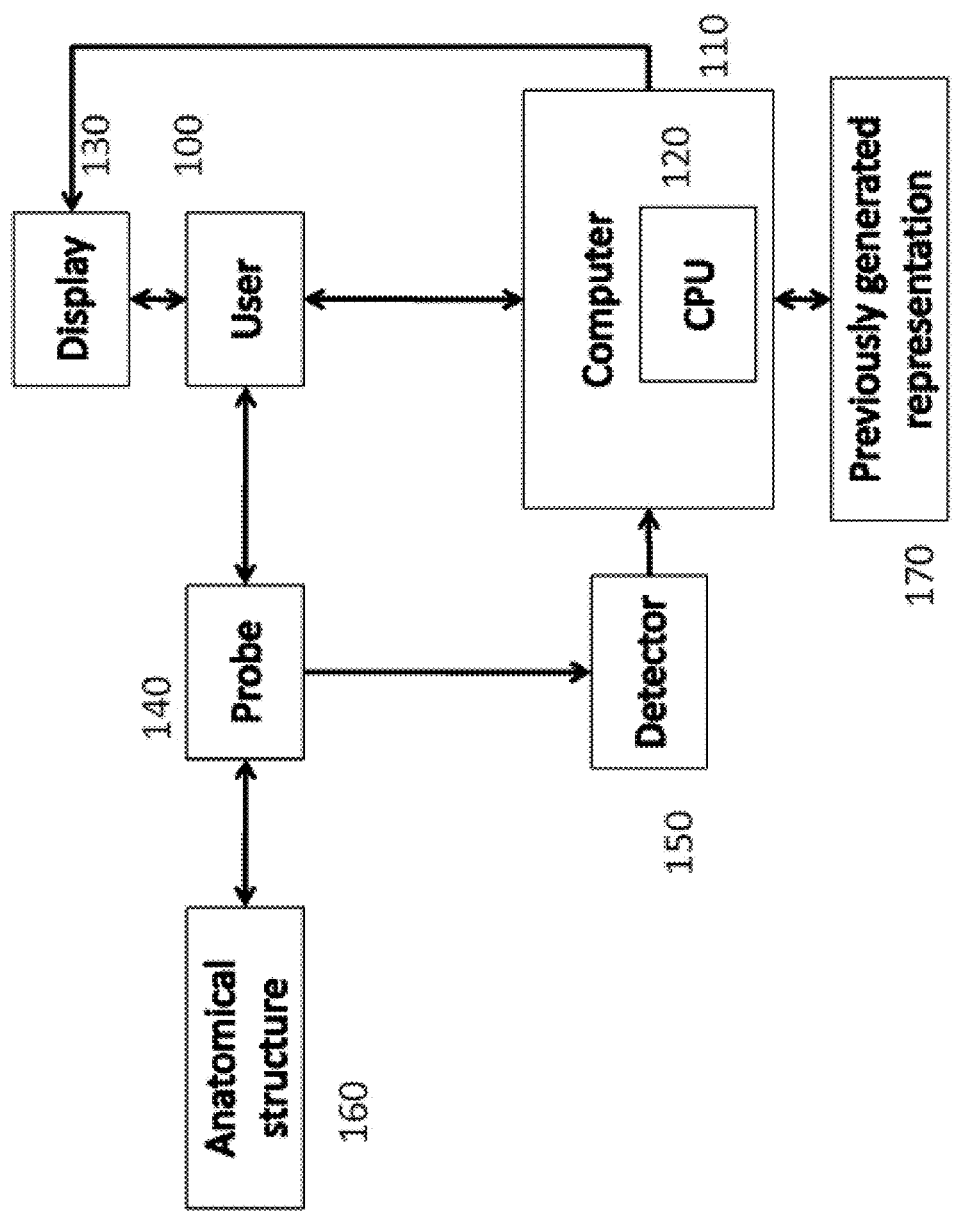
FIG. 1 illustrates an embodiment of a high level workflow according to the invention.

Described herein are methods, devices and systems for planning and executing image-guided, computer-assisted surgical procedures to achieve intra-operative alignment of anatomical structures with pre-operatively generated representations of the anatomical structures. The invention is particularly useful in planning and executing orthopedic surgeries, for instance coupling of a prosthesis to a long bone, such as a femur, tibia, humerus, ulna, and radius.

The present invention, however, is not limited to such robotic procedures and will be equally useful in manual surgical, diagnostic, and other medical procedures where it is necessary to align a pre-obtained image, or model, of an anatomical structure with the intra-operative position and orientation of the anatomical structure. Such manual systems and procedures include computer-assisted surgical procedures that employ optical surgical measurement tools, passive electromechanical devices, and the like.

In current clinical practice, the first step in image-guided, computer-assisted surgery is the generation of a representation of the anatomical structure of interest, usually as a set of medical images created using techniques like Computer Tomography (CT), Ultrasound (US) or Magnetic Resonance Imaging (MRI). These images are taken preoperatively and are utilized to plan the surgery. The plan and images are transferred to a computer associated with the operation room to guide the surgical procedure.

However, since the patients' anatomy has likely been moved after taking the preoperative images and before starting the operation, the position and orientation of the anatomical structure to be operated on may no longer match those of the pre-operatively generated representation. Therefore, matching the preoperative images to the actual patient's position and orientation in the operation room using an intra-operatively generated representation of the anatomical structure by means of a set of transformation parameters is critical. This matching process is known as registration.

Registration is a critical step in the planning and execution of computer-assisted robotic surgery. Inaccurate and unreliable registration could lead surgeons to operate on the wrong areas of patients. Hence, a reliable registration technique is imperative in image-guided computer-assisted surgery systems.

The registration process is performed by selecting a number of data points on the anatomical structure, and matching the position of the data points on the pre-operatively and intra-operatively generated representations. In current clinical practice, the data points are often limited in number, and are positioned on precisely defined locations, such as anatomical landmarks or surgically inserted markers.

Identifying the exact locations may be time-consuming and require an extensively trained and/or experienced user. Because of the criticality of the position of these marker points, the method is time consuming and prone to inaccuracies due to operator error.

To improve the accuracy of the registration, it is desirable to increase the number of data points, and to reduce the criticality of their location. Furthermore, it is desirable to perform the acquisition of the data points intra-operatively, and in an interactive, computer-guided process to increase the speed and efficiency of the data point acquisition.

Accordingly, it is an objective of the present invention to provide methods, systems and devices to improve the speed and reliability of the process of intra-operative registration of an anatomical structure to a previously generated representation of the anatomical structure.

With the development of increased computing speed and interface versatility it is now technically feasible to greatly increase the number of registration data points provided to a Central Processing Unit (CPU) of a computer. This has opened up the possibility of employing a user-computer interactive process of acquiring the registration data points. Such an interactive process may acquire data points, select correctly acquired data points, reject incorrect ones, and generally greatly increase the number of data points collected. As a consequence the risk of operator error and the time required to identify the exact location of the landmarks or fiduciary points may be reduced, and the quality of the registration process significantly improved. Additionally, the process may intra-operatively guide the user in the acquisition of the data points, thereby further increasing the speed, user-friendliness and reliability of the registration process. Since such a process may guide the user in the acquisition of data points until convergence of the intra-operative registration model with the pre-operative representation is achieved, the process may inherently be customized to patient- and user-specific parameters and preferences. The following description of preferred embodiments of the invention is not intended to limit the invention to these preferred embodiments, but rather to enable any person skilled in the art to make and use this invention.

Methods

An example of a high level workflow according to the present invention is shown in FIG. 1. A user 100 may direct an acquisition probe 140 to the surface of an anatomical structure 160. A sensor in the acquisition probe 140 may generate a signal from the surface, triggering acquisition of one or more data point(s) 305. The data point(s) 305 may not be restricted with respect to localization.

The position of the acquisition probe 140, corresponding to the position of the data point 305, may be detected by a detector 150 and communicated to a computer 110 having a CPU 120 capable of running a suitable computer algorithm. The computer may process the information from the detector 150 in relation to a pre-operatively generated representation of the anatomical structure 170. The process may be repeated for multiple data points 305 and anatomical structures. The computer may evaluate the aggregate of data points 305 and provide feedback to the user 100 about additional data points 305 to be acquired to achieve a match between the intra-operative position and orientation of the anatomical structure 160 and the pre-operatively generated representation 170. Additionally, upon evaluation of the aggregate of data points, the computer may assess the quality of the data points collected. For example, if a point or points appear to incorrectly represent the surface (e.g. the point is positioned an inappropriate distance above or below adjacent points) the point may be considered an outlier, and may be removed from the aggregate of points. Once an adequate match (Convergence) is achieved a signal may be sent to the user 100 via a display 130.

In preferred embodiments of the invention, the computer may be capable of providing feedback to a user 100 acquiring data points 305 in real time, and the interaction between the user 100 and the computer may allow an iterative process, in which the computer may guide the user 100 in the acquisition of additional data points 305 towards convergence of the registration of the surface of the anatomical structure 160 to the previously recorded representation 170.

Algorithms suitable for the embodiments of the present invention are preferably capable of identifying and rejecting bad data points 305, collecting suitable acquired data points 305, providing feedback to a user with regards to additional data points 305 to be acquired, determining when an adequate number of data points 305 has been collected to achieve convergence between the intra-operatively and the pre-operatively collected images of the anatomical structure, and signaling achievement of convergence to a user 100.

Suitable algorithms for the embodiments of the invention may include the Unscented Kalman Filter (UKF) algorithm.

The workflow of FIG. 1 is merely intended as an example of the scope of the invention, and is not intended as a limitation on that scope. Other workflows under the scope of the invention will be readily apparent to those with ordinary skills in the art.

Figure 2:
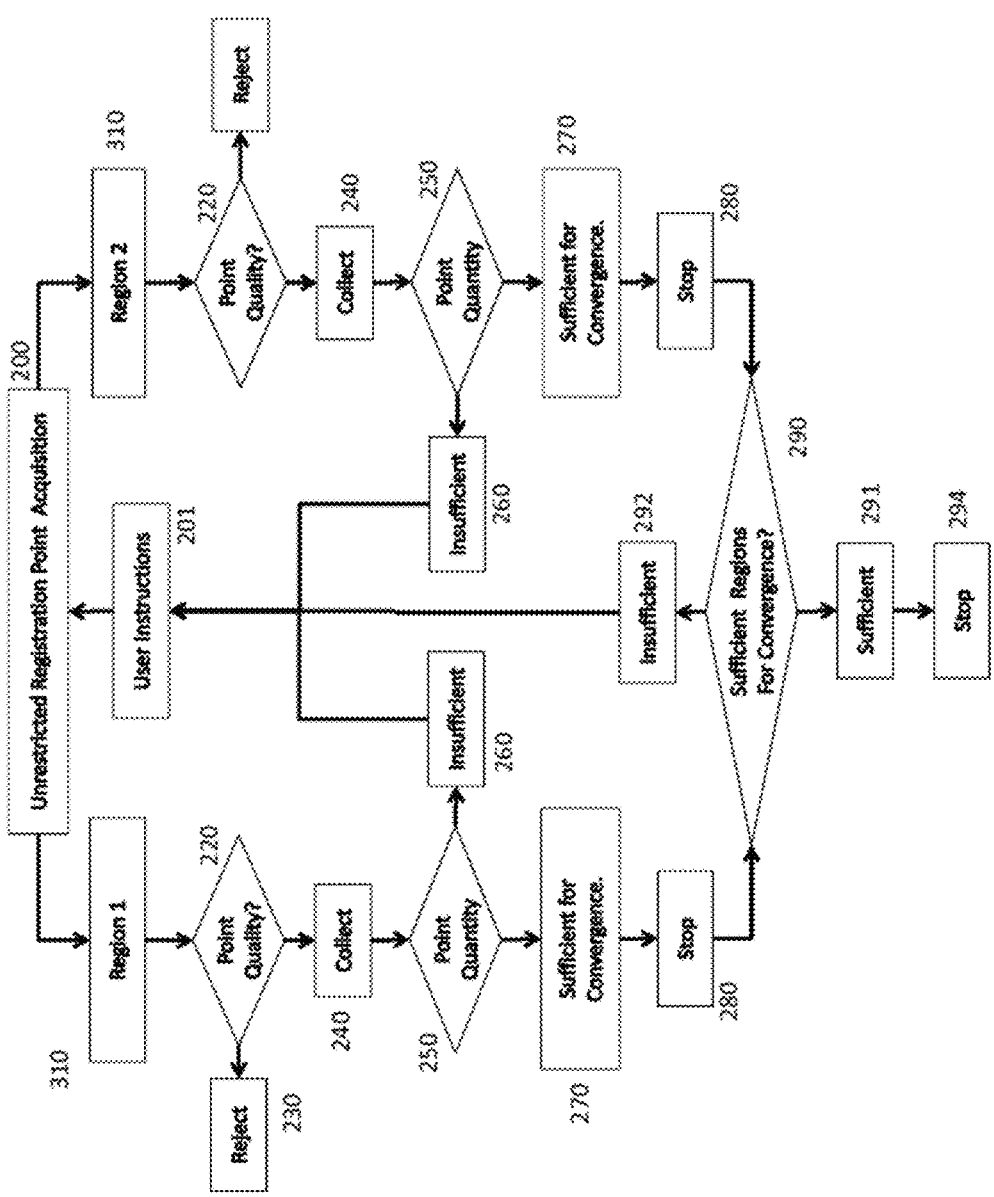
FIG. 2 illustrates a flow chart of a method for registering an anatomical structure according to the invention.

A flowchart of an exemplary embodiment of the present invention is illustrated in FIG. 2. Acquisition 200 of data points 305 unrestricted by localization on the anatomical structure may be performed on one or more regions 310. The quality of the data points 305 may be assessed 220, data points 305 of insufficient quality may be rejected 230 and data points 305 of sufficient quality collected 240. As described above, upon evaluation of the aggregate of data points, the computer may assess the quality of the data points collected. For example, if a point or points appear to incorrectly represent the surface (e.g. the point is positioned an inappropriate distance above or below adjacent points) the point may be considered an outlier (i.e. of insufficient quality), and may be removed from the aggregate of points. Additionally, an assessment 250 may be performed if sufficient data points 305 have been collected to achieve convergence of the registration of the anatomical structure with the previously recorded representation. If insufficient data points 305 have been collected 260, user instructions 201 may be generated to continue acquisition of data points 305. If sufficient data points 305 have been collected 270, the acquisition process may be stopped 280. The data point acquisition process may be performed on multiple regions 310. An assessment 290 may be made if sufficient data points in sufficient regions have been acquired and, in the case of insufficient regions 292 user instructions 201 may be generated, or, in the case of sufficient regions 291, the process may be stopped 294.

Accordingly preferred embodiments of the invention may include interactive methods for acquiring data points 305 and generating a registration of a surface of an anatomical structure, wherein a user provides information about data points 305 to a computer and receives feedback from the computer containing directions for continuing the process of data point acquisition in order to optimize the generation of the registration of the surface of the anatomical structure.

The flowchart of FIG. 2 is merely intended as an example of the scope of the invention, and is not intended as a limitation on that scope. Other embodiments will be readily apparent to those with ordinary skills in the art.

As illustrated in FIG. 1, in some embodiments of methods according to the invention a user 100 may acquire initial data points on the surface of an anatomical structure 160, and may send information about the data points 305 to a computer 110. The user 100 may employ a computer 110 to evaluate the quality of the data points 305, to reject data points 305 of insufficient quality, if any, and to collect the data points 305 of sufficient quality. As described above, upon evaluation of the aggregate of data points, the computer may assess the quality of the data points collected. For example, if a point or points appear to incorrectly represent the surface (e.g. the point is positioned an inappropriate distance above or below adjacent points) the point may be considered an outlier (i.e. of insufficient quality), and may be removed from the aggregate of points. The computer 110 may further be used to evaluate the quantity of data points 305, and to assess if sufficient data points 305 have been collected to achieve convergence of registration of the surface with a previously generated representation of the anatomical structure 170. The quantity of data points may be considered sufficient if a sufficient number of points have been collected to achieve convergence. Alternatively, or additionally, the quantity of data points may be considered sufficient to achieve convergence if a sufficient number of points have been collected in a sufficient number of locations or regions across the anatomical structure. For example, if several points are collected in a single or limited number of locations, the quantity of the data points may be considered insufficient even considering the large number of points collected. In other words, it is desirable for the data points collected to sufficiently cover the anatomical structure and/or key regions of the anatomical structure.

In some embodiments of the invention, the data points 305 on the surface of the anatomical structure 160 may not be restricted by localization. In some embodiments of the invention the computer 110 may automatically stop the process of data point acquisition once sufficient data points 305 have been collected.

In some embodiments of the invention, if insufficient data points 305 have been collected, the computer 110 may be used to generate instructions for additional data points 305 to be acquired, and the user 100 may continue acquiring data points 305 at least until sufficient acceptable data points 305 have been collected to achieve convergence of registration of the surface with the previously generated representation of the anatomical structure.

Registration of an entire surface of interest on an anatomical structure 160 may require a very large number of data points 305 to be collected. Some embodiments of the invention may advantageously allow a user planning the surgical procedure to design a more efficient registration process by dividing the surface of the anatomical structure 160 to be registered in multiple regions 310. In such embodiments the data points 305 may be acquired on a per-region basis, allowing a more structured and more efficient data point acquisition and surface registration process. In such embodiments, the computer may be capable to assess not only the adequacy of the number of collected data points 305 per region 310, but also to evaluate if sufficient regions 310 have been included to achieve convergence, and, if insufficient regions have been included, to generate instructions 201 for a user 100 to acquire additional data points 305 or to add additional regions 310. In such embodiments a region 310 for data point acquisition may be identified and anatomically defined, the area of the region 310 covered by acquired data points 305 may be calculated, and the percentage of the area covered by the data points 305 may be indicated by use of the algorithm.

Figure 3:
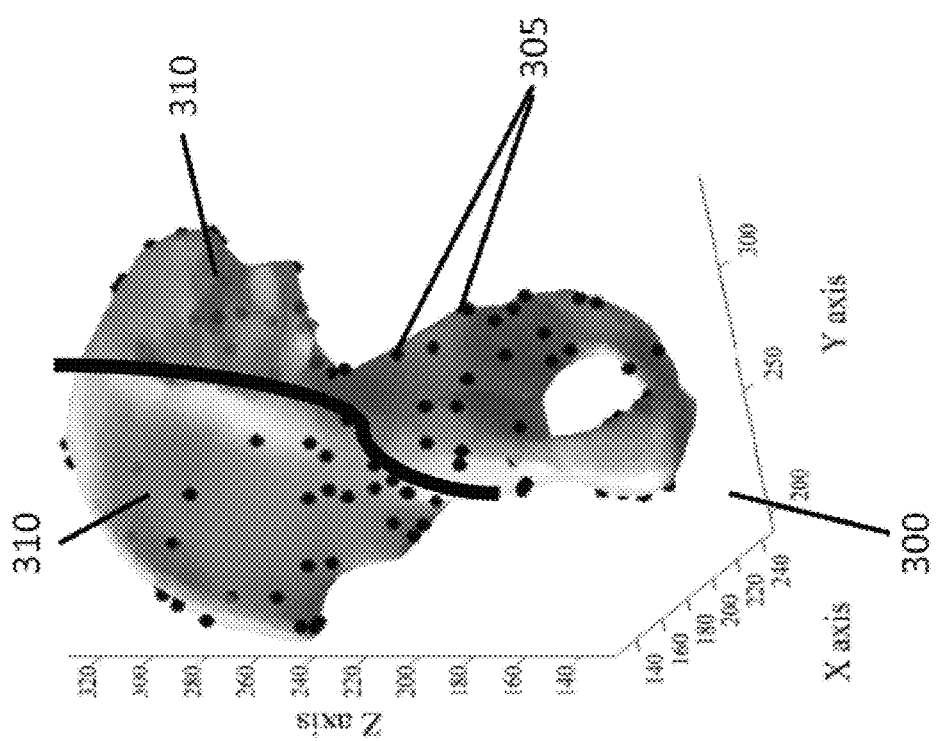
FIG. 3 illustrates a bone with regions and data points according to the invention.

FIG. 3 illustrates a bone with data points 305 and regions 310. In some embodiments of the invention the collected data points 305 represent at least one region 310 on the anatomical structure 160. In some embodiments of the invention the surface of the anatomical structure 160 may comprise multiple regions 310. In some embodiments of the invention, the computer may be used to evaluate if sufficient data points 305 in sufficient regions 310 have been collected to achieve convergence of registration of the surface with the previously generated representation of the anatomical structure 160.

In some embodiments of the invention, if insufficient data points 305 have been collected, the computer may be used for generating instructions 201 for acquiring data points 305 in additional regions 310, and a user 100 may continue acquiring data points 305 in additional regions 310 at least until sufficient data points 305 in sufficient regions have been collected to achieve convergence.

In some embodiments of the invention the process of acquiring the initial data points 305 may be performed intra-operatively. In some embodiments of the invention, the previously generated representation of the anatomical structure 170 may be generated pre-operatively.

A great advantage of modern computer technology is the speed with which computational operations can be performed, allowing the use of sophisticated algorithms like the UKF in real-time or near real-time. In some embodiments of the invention, this may allow a user 100 to perform the registration process in an interactive manner with the computer 110, where the computer may evaluate the quality and quantity of data points 305 acquired, and provide feedback and guidance to the user 100 about additional data points 305 to be acquired and additional regions 310 to be included.

Accordingly, in some embodiments of the invention employing the computer may be performed at least in part simultaneously with acquiring of the data points 305.

In some embodiments of the invention the anatomical structure 160 may be a bone or an assembly of bones, such as a skull or a pelvis.

Systems and Devices

Figure 4:
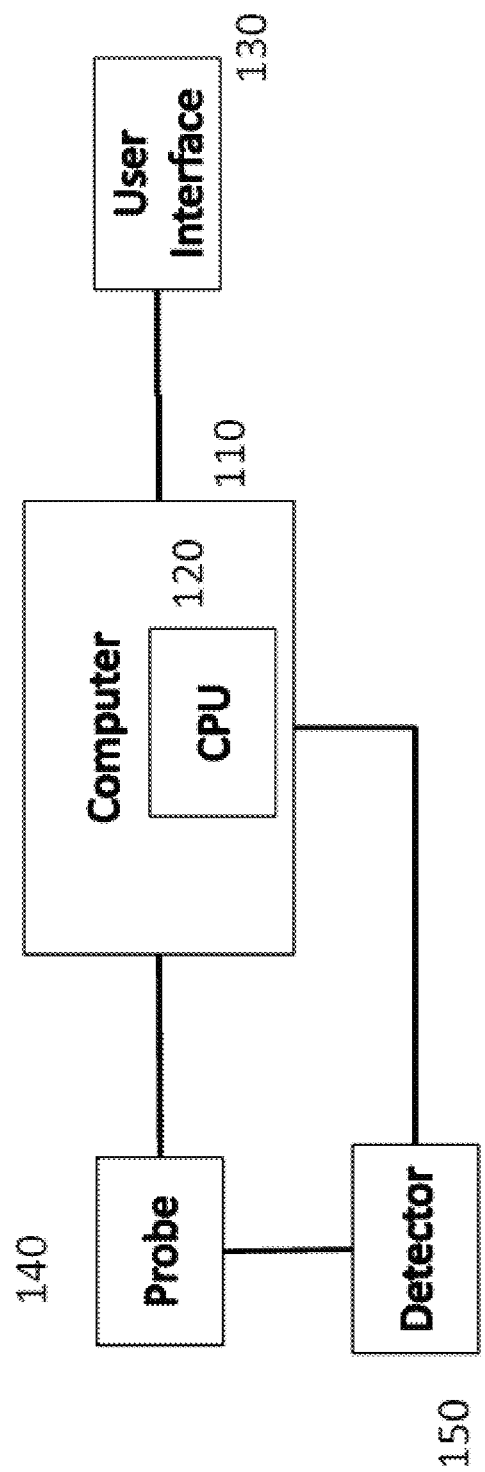
FIG. 4 illustrates an embodiment of a computerized system according to the invention.

A system for performing tasks is illustrated in FIG. 4, and may comprise a computer 110 having a CPU 120, an acquisition probe 140, a detector 150 and a user interface 130. The user interface may comprise multiple components, for example a display, a mouse and a keyboard. The system in FIG. 4 is merely included as an exemplary embodiment, and is not intended to limit the scope of the invention. More components than the illustrated ones may be included, and not all included components need to be present.

For instance, in some embodiments the acquisition probe 140 and the detector 150 may be combined in one component. In some embodiments, multiple probes 140 or other interfaces 130 may be present, such as a touch screen.

The computer 110 of the embodiments of the present invention may be any type of computer, like a desktop, laptop or tablet computer. The computer 110 does not have to be co-localized with other components of the system, but may be in communication through connections like a phone line or Internet connection.

In preferred embodiments, the computer may comprise a Central Processing Unit (CPU) 120 capable of executing functions associated with an algorithm suitable for the methods of the invention, such as the Unscented Kalman Filter (UKF). In some embodiments the CPU 120 may be of a dedicated design, exclusively configured to perform those functions. In other embodiments the CPU 120 may be capable of performing additional tasks in addition to being capable of the functions of the methods of the invention. Advantageously, such additional tasks may include Internet search capability, literature searching, communicating through e-mail and other Internet enabled communication means, calculations, and other tasks a user 100 may deem desirable. Alternatively, the CPU 120 may be of any other suitable design that is capable performing the functions necessary for the methods of the invention.

The invention is not limited to a specific number or type of CPU. The computer may contain a single CPU, or multiple CPUs or specialized CPU like a dual core CPU. The system is not limited to the use of a single computer. Under the scope of the invention, the system may employ multiple computers to perform the functions necessary for the methods of the invention.

During the acquisition of the data points 305, occasionally an erroneous data point may be acquired. Currently used algorithms are sensitive to multiple error sources, for instance misalignment of the acquisition probe, incorrect reading by the instrumentation used, initial misalignment of the position of anatomical structure, and noise in the measurement of the data points 305.

In preferred embodiments of the invention, the algorithm used for processing the acquired data points 305 may be capable of evaluating the quality of the acquired data points 305, rejecting incorrectly acquired data points 305, and collecting correctly acquired ones, thus making the procedure less prone to errors due to bad data points 305. As described above, the algorithm may assess the quality of the data points collected. For example, if a point or points appear to incorrectly represent the surface (e.g. the point is positioned an inappropriate distance above or below adjacent points) the point may be considered an outlier (i.e. of insufficient quality), and may be removed from the aggregate of points.

In some embodiments of the invention, matching of the intra-operatively created image of the anatomical structure to the pre-operatively created image may be based on surface topography as defined by the registered data points 305. The number of data points 305 required to achieve convergence between the pre-operative and the post-operative images may vary between anatomical structures and the quality and coverage (i.e. across multiple locations and/or regions of the anatomical structure) of the data points 305 collected. In preferred embodiments of the invention, the algorithm may be capable of determining when an adequate number of data points 305 has been acquired and processed to obtain such convergence. In alternative preferred embodiments of the invention, the computer may be able to process the data points 305 using the algorithm in real time, with a delay in signal output that is insignificant to a user acquiring the data points 305. In such embodiments, progress of the algorithm execution may be monitored towards convergence between the intra-operatively created registration of the surface of the anatomical structure and the pre-operatively created image or model, and, once convergence is reached, data points 305 acquisition may be stopped automatically or a signal may be sent to the user.

Such embodiments may allow for an efficient data points 305 acquisition process, in which a user may acquire a large number of data points 305, unrestricted by localization, until a computer signal is received that sufficient data points 305 have been acquired.

Additionally, the algorithm may be capable of generating instructions for a user with regards to additional data points 305 to be acquired to achieve convergence between the pre-operative and post-operative representations of the anatomical structure.

Also, technology used in current clinical practice often does not offer the possibility of reliably assessing the accuracy of the registration, leaving uncertainty for medical personnel. In preferred embodiments of the current inventions the algorithm used may be capable of providing a reliability assessment of the registration process, thus improving procedural accuracy and confidence of medical personnel in the results of the registration process.

In some embodiments the system may comprise a user interface, for example in the form of a display unit, a mouse and a keyboard 130. The interface 130 may be coupled to the computer 110, and may be capable of providing a user with a visible representation of the progress towards convergence. Additionally, guidance from the computer for the continued acquisition of data points 305 may be provided on a display. For instance, the display may show a 3D rendering of the pre-operatively generated representation 170 of the anatomical structure 160 as a basis for progress of the registration process and for guidance to further data point acquisition. The display device 130 may advantageously be a computer screen, but other displays, like printers, are included in the scope of the invention.

Accordingly, preferred embodiments of the invention may employ a computerized system. In general, the computerized system may include a computer having a CPU; an acquisition probe capable of acquiring data points 305 on the surface of the anatomical structure; a detector capable of detecting the position of the acquisition probe, and a user interface. In some embodiments, the CPU is capable of running a computer algorithm capable of receiving information about acquired data points 305 from a surface of an anatomical structure; evaluating quality of the data points 305; optionally rejection data points 305 of insufficient quality; collecting data points 305 of sufficient quality; evaluating quantity of collected data points 305 for sufficiency for registration of the anatomical surface; optionally generating user instructions for acquisition of additional data point, and generating a signal for stopping acquisition of data points 305 once sufficient data points 305 have been collected. As described above, upon evaluation of the aggregate of data points, the CPU and/or algorithm may assess the quality of the data points collected. For example, if a point or points appear to incorrectly represent the surface (e.g. the point is positioned an inappropriate distance above or below adjacent points) the point may be considered an outlier (i.e. of insufficient quality), and may be removed from the aggregate of points. As described above, the quantity of data points may be considered sufficient if a sufficient number of points have been collected to achieve convergence. Alternatively, or additionally, the quantity of data points may be considered sufficient if a sufficient number of points to achieve convergence have been collected in a sufficient number of locations or regions across the anatomical structure.

In some embodiments of the invention the data point acquisition may be performed with an acquisition probe. The user may register the surface of the anatomical structure by directing the acquisition probe to the surface. The acquisition probe may detect the presence of the surface based on various measurement modalities, including mechanical, optical and acoustic modalities. The acquisition probe may be operated manually by a user, or automatically, for instance by a computer assisted robot.

In some embodiments of the invention, the acquisition probe may trigger acquisition of data points 305 automatically, based on an internal sensor capability built into the acquisition probe. In other embodiments acquisition of data points 305 may be triggered manually by a user operating the acquisition probe, for instance by clicking a computer mouse or activating a button or switch.

In embodiments with a mechanical acquisition probe, the user may position the acquisition probe on the surface of the anatomical structure. In some embodiments the user may manually trigger acquisition of data points 305 based on tactile feedback of the acquisition probe. In some embodiments of the invention, triggering the acquisition of the data points 305 may be automated based on a change in the velocity profile of the probe, such as when the probe has stopped moving. In some embodiments of the invention triggering the acquisition of the data points 305 may be automated by including a sensor in the acquisition probe. In some embodiments the sensor may be an accelerometer. The accelerometer may be triggered by a change in velocity of the acquisition probe when the tip of the acquisition probe lands on the surface of the anatomical structure, for instance a bone. In some embodiments a force sensor may be included at the tip of the acquisition probe. In some embodiments a spring-loaded moveable post may be included at the tip of the acquisition probe. Landing the acquisition probe on the surface of a rigid anatomical structure may compress the spring, allowing the post to activate a switch in the acquisition probe. In some embodiments the sensor may be optical sensor, capable of detecting when the tip of the acquisition probe has reached the surface of the anatomical structure. In embodiments with an acoustic acquisition probe, the probe may be an ultrasound probe, which may allow non-invasive acquisition of data points 305.

In some embodiments of the invention, acquiring of data points 305 may be performed based on a signal from an acquisition probe. In some embodiments of the invention, manipulation of the acquisition probe may be performed manually. In some embodiments of the invention, manipulation of the acquisition probe may be performed automatically. In some embodiments of the invention, acquiring of data points 305 may be performed mechanically. In some embodiments of the invention, acquiring of data points 305 may be performed automatically. In some embodiments of the invention, acquiring of data points 305 may be performed with an acquisition probe having an accelerometer. In some embodiments of the invention, acquiring of data points 305 may be performed with an acquisition probe having a force sensor. In some embodiments of the invention, acquiring of data points 305 may be performed acoustically. In some embodiments of the invention, acquiring of data points 305 may be performed by ultrasound. In some embodiments of the invention, acquiring of data points 305 may be performed optically. In some embodiments of the invention, acquiring of data points 305 may be performed by laser.

FIG. 5 illustrates an exemplary embodiment of an automated acquisition probe and detector system according to the invention. An acquisition probe 490 with a probe housing 410 is shown over an anatomical structure 400. The acquisition probe has a tip 440 holding a spring-loaded moveable sensor post 450. Placement of the acquisition probe 490 onto the anatomical structure 400 brings the moveable post 440 in contact with the sensor 470 which may be connected to a computer wirelessly, or through wire 430. Probe housing 410 has a motion tracker target 420 facing the detector 480. Detector 480 tracks the movement of acquisition probe 490 and upon activation of sensor 470 sends a signal to the computer with information about the position of the data point 305 acquired at the tip 440 of the acquisition probe 490.

Detection of the motion and position of the acquisition probe may be achieved by a variety of detection means, such as optical or mechanical detection. In some embodiments the motion and position of an acquisition probe may be tracked by an optical motion tracker, such as the OPTOTRAK® Motion Capture Systems. In some embodiments the motion and position of an acquisition probe may be tracked with a displacement arm, as with an IMMERSION™ Microscribe 3D digitizer. Detection may be achieved through displacement of joints and segments of the displacement arm relative to a standard position and recorded on the computer for processing with the algorithm.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-assisted method of registering a surface of an anatomical structure to perform an image-guided surgical procedure, the method comprising:
   generating an image or model of the anatomical structure from pre-operative medical images by Computer Tomography (CT), Ultrasound (US), Magnetic Resonance Imaging (MRI), or a combination thereof;
   storing the image or model in a computer associated with an operation room to guide a surgical procedure;
   acquiring data points on the surface of the anatomical structure unrestricted by localization with a tracked acquisition probe;
   automatically matching, in real-time by the computer, the positions of the acquired data points to corresponding positions on the virtual representation of the anatomical structure while rejecting outlying data points that incorrectly represent the surface of the image or model of the anatomical structure and;
   collecting the non-rejected data points;
   computing, in real-time, if a sufficient quantity of non-rejected data points have been collected to achieve convergence of registration of the surface with the representation of the anatomical structure;
generating and displaying instructions to acquire additional data points on the surface if an insufficient quantity of non-rejected data points have been collected until convergence of registration of the surface with the representation of the anatomical structure is achieved; and
executing the image-guided surgical procedure on the anatomical structure converged with the representation of the anatomical structure.

2. A computer-assisted method of registering a surface of an anatomical structure, the method comprising:
generating an image or model of the anatomical structure from pre-operative medical images by Computed Tomography (CT), Ultrasound (US), Magnetic Resonance Imaging (MRI), or a combination thereof;
storing the image or model of the anatomical structure in a computer associated with an operation room to guide a surgical procedure according to the surgical plan;
acquiring data points on the surface of the anatomical structure unrestricted by localization with a tracked acquisition probe; and
employing a computer executing a surface recognition-based algorithm to:
automatically match, in real-time with the computer, the positions of the acquired data points to corresponding positions on the virtual representation of the anatomical structure while rejecting outlying data points that incorrectly represent the surface of the anatomical structure; and
collecting the non-rejected data points;
compute if a sufficient quantity of non-rejected data points have been collected to achieve convergence of registration of the surface with the representation of the anatomical structure; and
generate instructions to acquire additional data points if an insufficient quantity of non-rejected data points have been collected until convergence of registration of the surface with the generated representation is achieved; and
execute an image-guided surgical procedure on the anatomical structure converged with the representation of the anatomical structure.

3. The method of claim 2, wherein the computer automatically stops the process of data point acquisition once a sufficient quantity of the non-rejected data points has been collected.

4. The method of claim 2, wherein the data points represent at least one region on the anatomical structure.

5. The method of claim 2, wherein the surface of the anatomical structure comprises multiple regions.

6. The method of claim 5, further comprising:
employing the computer to:
evaluate if sufficient quantity of non-rejected data points in one or more regions have been collected to achieve convergence of registration of the surface with the representation of the anatomical structure; and
provide instructions for acquiring additional data points in a specific region if said specific region has an insufficient quantity of the non-rejected data points for convergence of registration of the surface with the representation of the anatomical structure to be achieved.

7. The method of claim 2, wherein employing the computer is performed at least in part simultaneously with acquiring of the data points.

8. The method of claim 2, wherein acquiring data points is performed intra-operatively.

9. The method of claim 2, wherein acquiring of data points is performed based on a signal from an acquisition probe.

10. The method of claim 9, wherein acquiring of data points is performed with an acquisition probe having an accelerometer.

11. The method of claim 9, wherein the acquired data points are acquired automatically when the acquisition probe contacts the bone as determined by a velocity profile of the acquisition probe.

12. The method of claim 9, wherein acquiring of data points is performed with an acquisition probe having a force sensor.

13. The method of claim 2, wherein acquiring of data points is performed acoustically.

14. A computer-assisted robotic system, comprising:
a robotic system for executing a surgical procedure on an anatomical structure having a computer with a CPU, the CPU being capable of running computer algorithms capable of:
assisting in the generation of an image or model of the anatomical structure from pre-operative medical images by Computed Tomography (CT), Ultrasound (US), Magnetic Resonance Imaging (MRI), or a combination thereof;
receiving information about acquired data points, unrestricted by localization, from a surface of an anatomical structure;
automatically matching, in real-time, the positions of the acquired data points to corresponding positions on the virtual representation of the anatomical structure while
rejecting outlying data points that incorrectly represent the surface of the anatomical structure;
collecting non-rejected data points;
computing if a sufficient quantity of the non-rejected data points have been collected to achieve convergence of registration of the anatomical surface with the representation of the anatomical structure;
generating user instructions for acquisition of additional data points;
generating a signal for stopping acquisition of data points once convergence is achieved; and
executing a surgical procedure on the anatomical structure converged with the representation of the anatomical structure; and
an acquisition probe capable of acquiring data points on the surface of the anatomical structure;
a detector capable of detecting the position of the acquisition probe; and
a user interface.

15. The system of claim 14, wherein the computer algorithm is based on a surface recognition-based algorithm.

16. An acquisition probe having a detection mechanism for detecting a data point on a surface of an anatomical structure, the acquisition probe being capable of automatically triggering acquisition of the data point by a computer, based on the position of the acquisition probe on the surface of the anatomical structure in the method of claim 1.

17. The acquisition probe of claim 16, wherein the detection mechanism is one of an accelerometer, a force sensor, a moveable post and an optical detector.

\* \* \* \* \*